United States Patent [19]

Milbank et al.

[11] Patent Number: 4,858,001

[45] Date of Patent: Aug. 15, 1989

[54] MODULAR ENDOSCOPIC APPARATUS WITH IMAGE ROTATION

[75] Inventors: Miles C. Milbank, San Ramon; Perry M. Williams, San Carlos, both of Calif.

[73] Assignee: High-Tech Medical Instrumentation, Inc., San Francisco, Calif.

[21] Appl. No.: 106,742

[22] Filed: Oct. 8, 1987

[51] Int. Cl.$^4$ .................. H04N 7/18; A61B 1/04; A61B 1/06

[52] U.S. Cl. ................................. 358/98; 128/6; 356/241; 358/229; 358/225; 433/29

[58] Field of Search .............. 358/98, 225, 229; 128/6; 433/29, 30, 31; 356/241

[56] References Cited

U.S. PATENT DOCUMENTS

| | | | |
|---|---|---|---|
| 3,051,166 | 8/1962 | Hounanian | 128/4 |
| 3,417,745 | 12/1968 | Sheldon | 128/6 |
| 3,622,785 | 11/1971 | Irwin | 378/99 |
| 3,884,222 | 5/1975 | Moore | 433/31 |
| 4,260,376 | 4/1981 | Litel | 433/29 |
| 4,277,168 | 7/1981 | Oku | 346/241 |
| 4,468,197 | 8/1984 | Provost | 433/30 |
| 4,479,499 | 10/1984 | Alfano | 433/29 |
| 4,629,425 | 12/1986 | Detsch | 433/29 |
| 4,667,229 | 5/1987 | Cooper | 358/98 |
| 4,727,416 | 2/1988 | Cooper | 358/98 |
| 4,757,381 | 7/1988 | Cooper | 358/98 |

*Primary Examiner*—Howard W. Britton
*Attorney, Agent, or Firm*—Townsend and Townsend

[57] ABSTRACT

A hand held endoscopic apparatus consists of a body, a camera and a removable and interchangeable objective element capable of presenting an image of an object to the camera. The objective element may be either rigid, or deformable, and may enable viewing of an image at varying angles to the longitudinal axis of the handpiece. The endoscope is capable of presenting an image for real-time viewing or for recording and play back at a later time. The camera is rotatably mounted within the body to allow rotation of the image presented for viewing. The endoscope is fully immersible in liquid media, for example sterilizing liquid, and is provided with an optically transparent sheath capable of isolating the endoscope from the working environment.

19 Claims, 5 Drawing Sheets

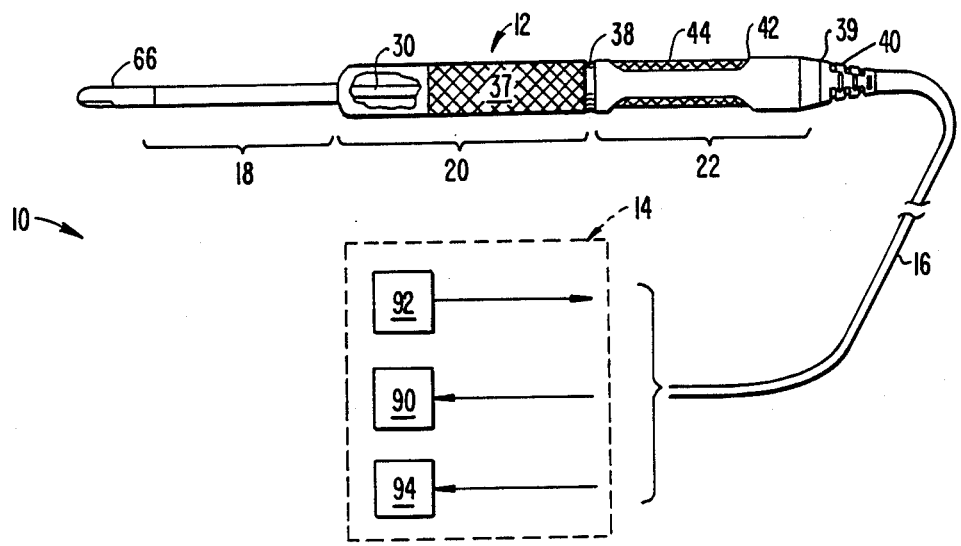
FIG._1.
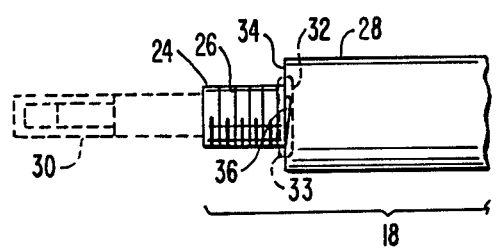
FIG._2.
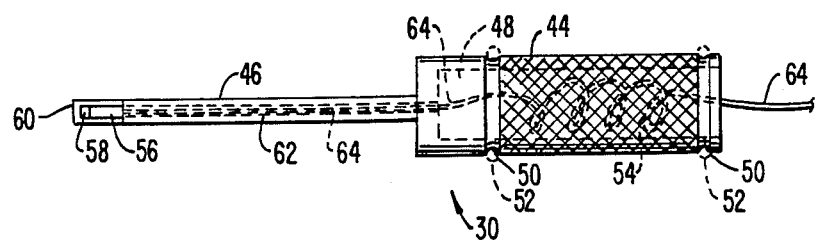
FIG._3.

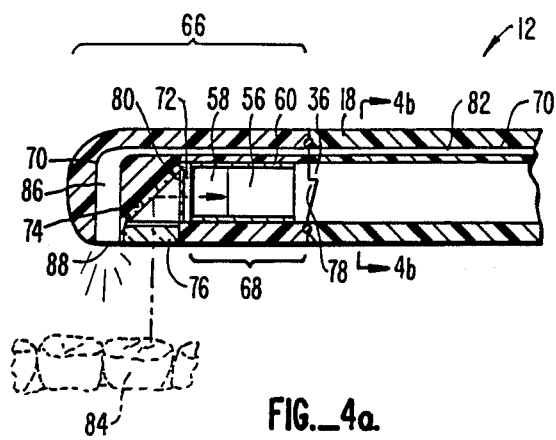
FIG._4a.
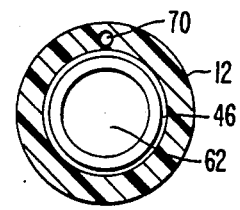
FIG._4b.
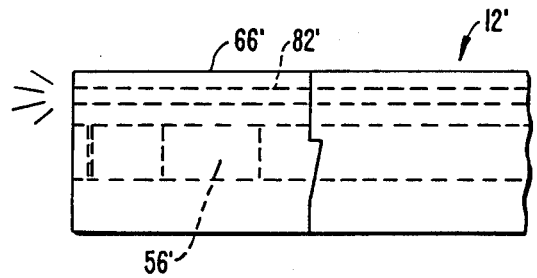
FIG._5.
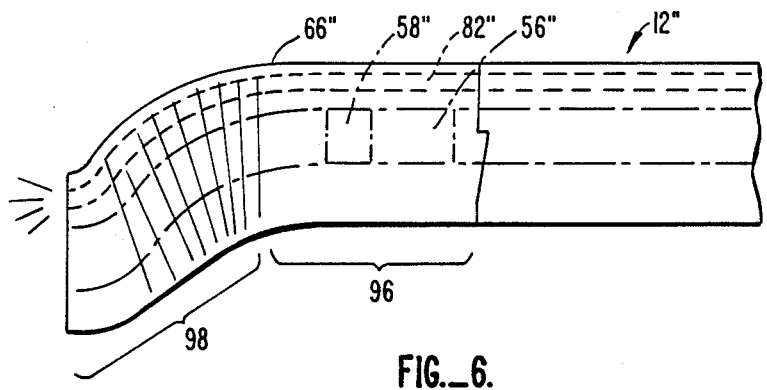
FIG._6.

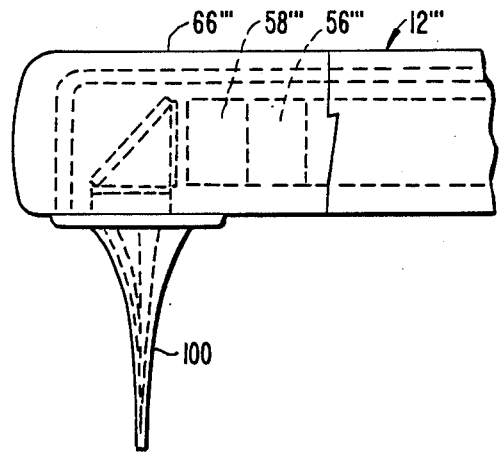
FIG.__7.
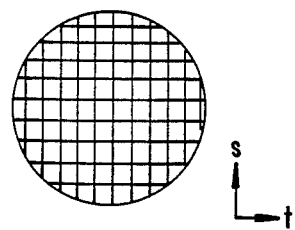
FIG.__8a.
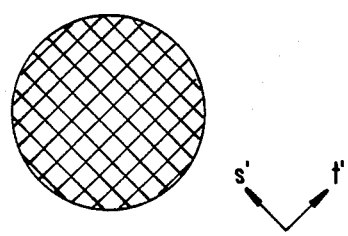
FIG.__8c.
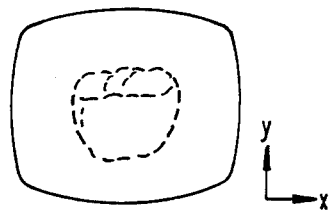
FIG.__8b.
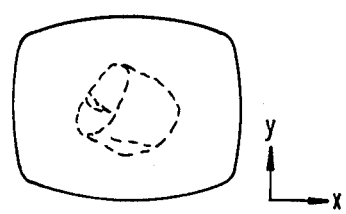
FIG.__8d.
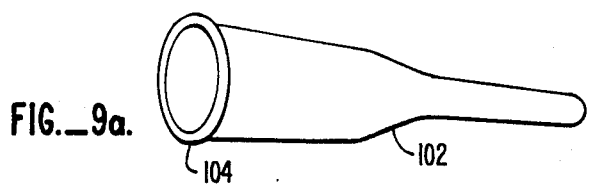
FIG.__9a.
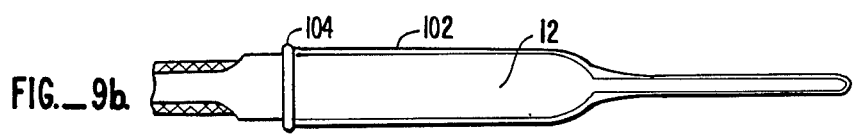
FIG.__9b.

MODULAR ENDOSCOPIC APPARATUS WITH IMAGE ROTATION

BACKGROUND OF THE INVENTION

1. Field of the Invention

The present invention relates generally to the field of endoscopic apparatus, and more particularly to endoscopes having modular connection for varying attachments and which are capable of rotating the image they present for viewing.

2. Description of the Prior Art

Endoscopy is a well known technique for viewing the internal region of a body not otherwise viewable. Such viewing is accomplished by introducing into the body an endoscope capable of optically communicating visual information regarding the interior of the body to a viewer or to video imaging equipment. The endoscope typically is a long, slender body with an image capturing portion at one end (the distal end) and a handle or other manipulating means at the other end (the proximal end). The endoscope typically includes various lenses, a fiber optic cable light source, and a camera. The camera is often located in the proximal end since in many cases the camera is larger than the area into which a viewing device may be located (i.e., the camera is larger than the diameter of the endoscope body). The video imaging equipment includes various video processing devices, a video monitor and/or video recorder which is capable of presenting video information received from the endoscope to a viewer. Thus, a video record of a relatively inaccessible region of the body could be viewed live or from recorded tape.

Advances in the microminiaturization of charge-coupled devices (CCDs), and similar solid state imaging hardware have made possible the reduction in size of the electro-optical endoscope. In addition, the wide variety of available shapes and configurations of endoscope bodies, and the development of flexible endoscopes, allow penetration into more convoluted interior regions of a body. This type of endoscopic probe has enabled deeper penetration and viewing of internal regions of, inter alia, the human body. The advent of monolithic CCD arrays and similar image hardware have also improved the image resolution attainable by endoscopic imaging techniques.

Endoscopes have found applications in a wide variety of disciplines, including dentistry, medicine, mechanical repair, aerospace applications, etc. - anywhere there is a need for remote viewing of a small, inaccessible region and/or recording what is seen. Often, activity is required in an area which is not directly viewable. For example, the medical practice of arthroscopic surgery, certain cardio-surgical procedures, etc., are done with remote instruments through the smallest possible opening in the patient. These procedures, which could not be accomplished without a clear view of the work area, are done using the required instruments in conjunction with an endoscope - the operation being done via a video monitor.

In the practice of dentistry, the X-ray machine has been the predominant imaging tool used to record and view dental and periodontal structure. Hand held tools having mirrored surfaces provide visual access by the dentist to many, but not all areas of the mouth not directly viewable. Such tools, of course, have the further limitation that they provide only a small image, and, were such desired, they offer no capability to provide a permanent record of what the dentist sees. Of particular relevance to the present invention are dental applications of endoscope technology, however the significance of the present invention to other applications of endoscopic technology must not be overlooked.

Certain devices are finding their way into the market which allow a dentist to both view regions not directly viewable and to record and monitor any region within the patient's mouth. These devices are improving in versatility and accuracy, but still there are significant limitations in the state-of-the-art. For example, the existing art is incapable of providing for varying the field of view and/or angle of view of the device to suit different applications and needs; is incapable of providing adequate illumination of the imaging target area; cannot be adequately sterilized (to prevent cross-contamination); is incapable of rotatably presenting the image to vary the relative up/down orientation; etc.

Thus, there is a present need in the art for an endoscopic apparatus capable of providing for varying the field of view and/or angle of view of the apparatus to suit different applications and needs, which is capable of rotatably presenting an image for viewing, and which is capable of a high degree of sterilization.

SUMMARY OF THE INVENTION

According to a preferred embodiment of the present invention, an endoscope is provided, which is particularly well suited to dental applications, having interchangeable, modular image-gathering elements (or objective elements) to accommodate a variety of applications, a solid-state miniature camera capable of generating video images for real-time viewing and/or recording by a video recorder, the camera being rotatable relative to the target area so as to rotate the image produced relative to the viewer, and further having provisions for securely receiving a sterile or medically clean sheath to aid in the prevention of cross-contamination.

Each objective element is generally comprised of a lens or lenses, light source projection optics, and optical interconnection for connecting the objective element to a handpiece. The objective element may be flexible, malleable, or rigid and may be of a variety of sizes and shapes to accommodate varying requirements of the user. Examples of objective elements include mirror and lens arrangements for viewing an image which is located at an angle such as 30, 60 or 90 degrees to the longitudinal axis of the handpiece, arrangements of lenses and fiber-optics to give a flexible or curved objective element capable of viewing otherwise inaccessible or hidden regions, etc.

The handpiece is comprised of a hollow or tubular body portion rotatably carrying a central shaft upon which is mounted a video camera arrangement such as a CCD mosaic chip camera, and a connection element capable of receiving an optical connection from the objective element. Provision for immersing the endoscope in a sterilizing solution without affecting the electrical componentry or interconnections is made, for example, by isolating the camera in an optically clear housing, and isolating the interior of the body with O-rings between the body and shaft. A standard ACMI light fitting (or equivalent) may be provided where the light source is to be a fiber-optic connection of a type commonly used in the art. The body has one or more openings that allow manual rotation of the shaft (and, hence, the camera) relative to the body.

The output of the chip camera is such that it may be directly input to one of a number of generic video endoscopy systems. Such systems are capable of providing real-time viewing of an image, and optionally may be capable of making a video record of the image on tape or the like.

Provision is made for receiving a sterile or medically clean, disposable, optically clear sheath around the endoscope in order to minimize cross-contamination from one patient to the next. The sheath is provided with a collar which fits into a circumferential recess in the body to hold it firmly in place while the endoscope is in use.

These features, as well as others, will become more readily apparent from the following detailed description of the preferred embodiment when read in conjunction with the illustrative embodiment in the accompanying drawings.

BRIEF DESCRIPTION OF THE DRAWINGS

FIG. 1 illustrates an endoscopic system according to a preferred embodiment of the present invention;

FIG. 2 details the arrangement of the objective receiving section of the endoscope handpiece according to a preferred embodiment of the present invention;

FIG. 3 details the shaft, handle and camera arrangement according to a preferred embodiment of the present invention;

FIGS. 4a and 4b illustrate the interrelationship of camera and objective element, and provision for integral light source;

FIG. 5 shows an example of one variation to the objective element of the preferred embodiment;

FIG. 6 shows another example of a variation to the objective element of the preferred embodiment;

FIG. 7 shows yet another example of a variation to the objective element of the preferred embodiment;

FIGS. 8a through 8d illustrate the relationship between camera orientation and image orientation; and FIGS. 9a and 9b illustate a sheath used to prevent transfer of contaminants to the area in which the endoscope is being used.

DETAILED DESCRIPTION OF THE PREFERRED EMBODIMENT(S)

Referring initially to FIG. 1, an endoscopic system 10 constructed according to a preferred embodiment of the teachings of the present invention is shown. System 10 comprises endoscope handpiece 12, video imaging equipment 14, and interconnection cable 16. The elements of system 10 will each be described in detail below, beginning with handpiece 12.

Handpiece 12 consists of basically four sections, objective receiving section 18, central body section 20 and orientation control section 22, and camera and lens carrying shaft 30. Shown in detail in FIG. 2 is a portion of objective receiving section 18. Section 18 is a longitudinal, tubular section capable at one end of removably receiving an objective element (not shown). In the presently described preferred embodiment, objective receiving section 18 includes a first tubular section 24 of a first diameter, having external helical threading 26 at one extremity as means for removably receiving the objective element. Other attaching means, such as bayonette-type mounts, slide mounts, etc. may serve equally well the task of securing an objective element to handpiece 12; however. First section 24 is coaxial and contiguous with a second tubular section 28 of a diameter larger than that of first section 24. Each of first and second sections 24, 28, respectively, are capable of receiving a shaft 30 (shown in phantom) in their interiors.

At the juncture of first and second sections 24, 28 an annular recess 32 is provided, extending part-way into each of first and second sections 24, 28 for securely receiving O-ring 33 (shown in phantom), providing a seal between the exterior and interior of handpiece 12 when an objective element (not shown) is secured to handpiece 12 (the purpose of which is described in detail below).

Face 34 where first section 24 adjoins second section 28 lies basically in a plane perpendicular to the common longitudinal axis of first and second sections 24, 28, respectively. Face 34 is provided with a wedge-shaped notch 36 inclined roughly parallel with the pitch of helical threads 26. The depth of notch 36 is slightly less than the spacing between adjacent threads. Notch 36 provides a stop mechanism for the objective element (not shown) which will be threaded onto first section 24, it's pitch and depth allowing a complementary notch in the objective element to be received in it, indexing the objective element into precise position (as will be further elaborated upon below). In keeping with the spirit of the present invention, many other indexing means are equivalent in result to the above-mentioned notch arrangement, including sliding lock and pin arrangements, click-stop arrangements, etc., when helical threading is used as the means for mounting the objective element to handpiece 12. Of course, when other types of mountings are employed, other solutions to indexing the objective element and handpiece become apparent.

The diameter of second section 28 will preferably be in the range of 4 mm to 10 mm, and first section 24 will be of a suitable smaller diameter, within a range of 2 mm to 5 mm for example. The length of objective receiving region 18 (i.e., the combined length of first and second sections 24, 28) is typically 65 mm, with first section 24 being typically 10 mm to 15 mm in length.

Secured to, or integrally formed with objective receiving section 18 opposite first section 24 is central body section (body section) 20 (returning to FIG. 1), which is generally tubular for receiving shaft 30 therethrough. The function of body section 20 is to provide a user with a gripable surface to facilitate manipulation of handpiece 12. To this end, body section 20 is of a slightly larger diameter than second section 28, a diameter on the order of 10 mm to 15 mm. At an end of body section 20 opposite objective receiving section 18 is an annular groove 38. The total length of body section 20 is then that length between objective receiving section 18 and groove 38, being in the range of 40 mm to 50 mm. Groove 38 is provided to receive a collar in a protective sleeve (which is not shown in FIG. 1, but which will be described in detail below). To further facilitate manipulation of handpiece 12, body section 20 is provided with a knurled surface 37 along a major portion of its length.

Extending from groove 38 to an open end 39 of handpiece 12 farthest from objective receiving section 18, where there is located a cable strain relief 40, is orientation control section (control section) 22, a roughly tubular section of similar diameter to body section 20. Control section 22 has one or more cut-away sections 42, in the form of elongated openings extending part way along the length of and part way around the circumference of control section 22. Cut-away sections 42 expose a portion of shaft handle 44 to allow rotation of the shaft within handpiece 12. As will be described in further detail, this rotation of shaft handle 44 (and consequently shaft 30) allows rotation of an image presented to a viewer. Many other ways of rotating shaft 30 are feasible, such as a knob connected to shaft 30 at its end, etc. beyond that being described as the preferred embodiment.

Shaft 30 is shown, for illustration purposes, isolated from handpiece 12 in FIG. 3. Two basic elements make up shaft 30, namely shaft handle 44 and adjoining camera-carrying section 46. Shaft handle 44 is roughly tubular in shape and of a first diameter, having a hollow region 48 therein for receiving wiring 64 (described below). Region 48 is provided with a teflon lining to prevent wiring 64 from catching or snagging and breaking any electrical connections or limiting rotation of shaft 30. The diameter of handle 44 is such as to allow it to rotatably fit within body section 20 and control section 22. The wiring enters a first end where handle 44 adjoins section 46, and exits the opposite end. A pair of annular grooves 50 are provided in the exterior of of handle 44 for receiving O-rings 52 (shown in phantom) which provide both a seal between the exterior and interior of handpiece 12, and bearing surfaces allowing shaft 30 to rotate within handpiece 12. The purpose and function of the seal, specifically with regard to O-rings 52, to allow immersion of handpiece 12 into a liquid without affecting the electronics or optics it carries, will be described in detail below. Handle 44 is provided with knurled section 54 to allow a user to firmly grasp and rotate it. This, as will be illustrated, results in rotation of an image presented to the viewer.

Section 46 is likewise roughly tubular in shape and coaxial with handle 44, but of a diameter smaller than that of handle 44. The diameter of section 46 is such as to allow it to rotatably fit within section 18. Secured to the end of section 46 opposite the end at which section 46 adjoins handle 44 is camera 56 and lens arrangement 58, each subject of further description below, positioned inside housing 60. Housing 60 is coaxially mounted to section 46 and is roughly tubular in shape, having one open end which sealingly secures to section 46 and one closed end opposite the open end which fits within an objective element (not shown). Camera 56 and lens arrangement 58 are roughly cylindrical in shape, coaxially mounted by means of adhesive or the like to section 46, and of an outside diameter so as to fit within housing 60. Housing 60 and section 46 are of a length such that at least a part of housing 60 extends beyond the end of first section 24 of objective receiving section 18, as shown in FIG. 2, for being inserted into an objective element (not shown).

The above description of shaft 30 being detached from handpiece 12, as shown in FIG. 3, is purely for illustrative purposes, and for description hereafter it is to be assumed that shaft 30 is installed within handpiece 12. So installed, shaft 30 is able to rotate within handpiece 12 around the longitudinal axis thereof, while being relatively firmly secured therein to prevent movement other than rotation along that longitudinal axis. This is accomplished, as previously mentioned, by O-rings 52 positioned in grooves 50. To further secure shaft 30 in handpiece 12, grooves (not shown) for receiving O-rings 52 may be provided in the interior wall of handpiece 12 corresponding to grooves 50 in handle 44.

Returning to FIG. 3, camera 56 and lens arrangement 58 are sealed within housing 60 such that section 46 carrying housing 60, camera 56 and lens arrangement 58 may be immersed in a liquid such as a sterilizing agent, etc., without interfering with the function of either. Section 46 is provided with a hollow region 62. Camera 56 will have connected to it a number of lead wires 64 which travel through hollow regions 62 and 48, exit handpiece 12, and are ultimately connected to an image processing system 14, shown in FIG. 1. Wiring 64 is coiled in hollow region 48 to provide stress relief and to help prevent catching or snagging which could break internal electrical interconnections and/or inhibit rotation of shaft 30. To prevent shorting or interference with the operation of camera 56 and lens arrangement 58 when immersed in liquid sterilizing agent, hollow regions 48 and 62 are sealed in handpiece 12 in a waterproof manner.

Camera 56 is preferably a high-resolution, light-sensitive charge coupled device (CCD), of a type readily available from a large number of manufacturers. For a detailed discussion of the nature and function of CCD cameras see Janesick and Blouke, "Sky on a Chip: The Fabulous CCD," Sky and Telescope, Sept., 1987, p. 238. Camera 56 in the presently described embodiment is monochromatic, although hybrid color CCD chips are equally applicable, being in the advanced stages of commercial development. When using a monochromatic CCD camera, color may be simulated by strobing light of predetermined frequency bandwidths on the image to be viewed, then displaying the image one frequency bandwidth at a time at a sufficiently high rate so that each appears to a viewer to be on simultaneously. Such color synthesis is well known in the art, and in use in analogous equipment available in the market place.

Securing to section 18, as shown in FIG. 4a, is an objective element 66. The illustrated objective element 66 is capable of bending the path the image to be viewed takes by 90 degrees while providing illumination of the image for an improved view. Other embodiments of objective elements 66', 66" and 66" (FIGS. 5, 6 and 7 respectively) will be described hereafter. Objective element 66 includes camera and lens receiving section 68, fiber-optic bundle receiving channel 70, immersion fluid receiving region 72 (defined by the closed end of housing 60 and transparent wall 80), mirror 74, and protective cover - lens arrangement 76. Further, objective element 66 is provided with an indexing notch 78, as a complementary notch to notch 36, described above and transparent wall 80.

In operation, objective element 66 is snugly secured to section 18 against O-ring 33 located in recess 32, indexed into a predetermined position by notches 36 and 78. Extending from an external light producing source (not shown) to handpiece 12 is a light transmission cable, for example fiber-optics, which may be carried be cabling 16. Handpiece 12 is provided with internal light transmission cabling 82 routed in receiving channel 70 (see also FIG. 4b), again for example fiber-optics, which extends along the length of handpiece 12 to the tip end of section 18. The interconnection between the light source and the handpiece may be by one of a wide variety of connections, including the commonly utilized ACMI light fitting. The terminus of internal cabling 82 in handpiece 12 is at an optical connection for transmitting light to objective element 66. Likewise, objective element 66 is provided with light directing optics 86 which terminates at one end at a light projecting lens 88, and at the other at an optical connection corresponding to that provided in handpiece 12. The optical connection comprises basically two abutting surfaces, one in handpiece 12, the other in objective element 66, capable of optically communicating with one another when placed in close proximity. Thus, when objective element 66 is snugly secured to handpiece 12, indexed into its predetermined location by notches 36 and 78, optical connection is made between the two and light is transmitted from its external source to appropriate optics located in objective element 66, providing illumination of the image to be viewed.

The image to be viewed, illuminated as described above, or by other means, must be made incident upon camera 56. Camera 56 operates to produce electrical signals corresponding to the image incident thereupon, when that image is incident generally perpendicular to the plane of the camera face (i.e., in a direction parallel to the longitudinal axis of handpiece 12). When it is desired to view an image perpendicular to the longitudinal axis of handpiece 12 the image must be bent or directed into the proper plane. To that end, an image of the desired object 84 is caused to pass by reflective mirror 74 from its plane perpendicular to the longitudinal axis of handpiece 12 into a plane parallel with the longitudinal axis of handpiece 12. In order to protect mirror 74 from contamination and debris which could damage it or impair the image it reflects, an optically clear protective cover and lens arrangement 76 is positioned between object 84 and mirror 74. It should be noted that while mirror 74 is capable of bending the path of the image to be viewed, many other means for accomplishing such bending are available, including, fiber-optic bundles, refractive lenses, etc.

Between camera 54 and mirror 74 there is provided focussing optics comprising a lens arrangement 58. As mentioned above, both camera 56 and lens arrangement 58 are sealingly secured in housing 60, the focus of lens arrangement 58 being preset or adjustable.

Because the surface area of camera 56 is relatively small and because mirror 74 is inclined relative to the surface of camera 56, camera 56 must have as wide a field of view as possible in order to collect sufficient light to produce an adequate signal. In order to increase the aperture of view of camera 56, and to provide improved image collection, a region 72 may be provided for receiving immersion lens fluid between mirror 74 (or equivalently, transparent wall 80) and lens arrangement 58 (or equivalently the closed end of housing 60). Many immersion lens fluids are useable in such an arrangement, with the characteristics that they have a high index of refraction, are chemically inert, and tend not to creep or leak from region 72.

Object element 66 may be one of a wide variety of arrangements of angle, length, diameter, flexibility, field of view, depth of field, etc. It may be of a small diameter, as small as 0.3 mm for root canal examination (e.g.), and of virtually any practical length, for example 2 mm to 20 mm, or longer. As well, the view angle of objective element 66 may be fixed or variable.

In operation, the endoscope as described above is connected to one of several commercially available video monitoring systems 90 (referring here to FIG. 1) which may include a light source 92 and recording device 94 (e.g., video recorder, digital recorder, etc.). The operator simply directs objective element 66 at the object to be viewed 84. The object to be viewed 84 is illuminated by light exiting fiber-optic bundle 86 at lens 88, and an image of object 84 is transmitted to camera 56. Camera 56 generates an electric signal representing the image which is transmitted by cable 16 to video monitoring system 14. Video monitoring system 14 may present the images for immediate viewing, record the images for later viewing, or both.

Thus, an easily manipulable video endoscope is provided, which, although particularly well suited to dental applications, may be used for video imaging of internal portions of the human body, or of areas of other objects not normally visible due to their location. A doctor, for example, may use the endoscope in standard arthroscopic procedure. The endoscope could be used to view behind an internal organ, such as the heart, during an operation, such as open heart surgery. It should be immediately apparent that the above-mentioned examples are merely illustrative of the multitude of possible applications of the present invention, its versatility partly based on the modularity or useability of a wide variety of objective elements.

Turning to FIG. 5, an alternate embodiment of objective element 66' is shown. In this embodiment, the focus of the optics contained therein is at 0 degrees to the longitudinal axis of the handpiece 12'.

The angle of focus in this embodiment is controlled by the position of the optics. Light is cast upon the object to be viewed by fiber-optic bundle 82' and the image translated into electrical signals by camera 56' as described above.

FIG. 6 shows an additional embodiment of objective element 66" wherein it is in the form of a flexible member moveable to an infinite number of focus positions. Objective element 66" comprises two regions, a rigid region 96 wherein is located camera 56", lens arrangement 58", each functioning as described above, and a flexible region 98, capable of transmitting the image to camera 56" by way of fiber-optics, etc.

FIG. 7 illustrates another embodiment of objective element 66''' designed to be placed in the opening of a root canal or similarly sized openings. The operative tip 100 of element 66''' reduces the focal area to a very small diameter, on the order of several hundredths of a millimeter. Element 66''' is very similar to that described as the preferred embodiment above, except insofar as operative tip 100, reducing both the image collection function and the light projection function by means well known in the art, for example reducing fiber-optics or graduated refractive index lenses, is added to the element.

The embodiment of handpiece 12 described above allows the user to rotate the image presented on a video screen, as demonstrated by FIGS. 8a–8d. Camera 56 has an intrinsic orientation as indicated by the camera axes labelled s and t of FIG. 8a. When an image is incident on camera 56 in a first orientation it presents the image to a monitor in a first orientation relative to the monitor, as indicated by the monitor axes labelled x and y in FIG. 8b. When camera 56 is rotated to a new orientation, as shown by camera axes s' and t' in FIG. 8c, relative to the monitor axes x and y the image presented thereby is rotated an equal amount as shown by FIG. 8d. Since, in the above described embodiment, camera 56 is secured to rotatable shaft 30, which may be rotated by the user at handle 44, the camera is directly rotatable by the user. In this way the endoscope of the present invention is capable of rotating the image it presents to a monitor, providing increased versatility and ease of use. Stopping means (not shown) is provided in handpiece 12, for example a pin and guide, threaded stop, or other well known stopping means, to limit the total rotation to 360° or less. This stopping means is provided so that camera 56 is not overrotated, causing a break in the electrical interconnections or interference with the smooth rotation of shaft 30 in handpiece 12.

Handpiece 12 is capable of being fully immersed in a liquid, such as a sterilizing agent, without damaging the optics or electronics it carries. This is accomplished by providing O-ring seals wherever there is rotatable interconnection or opening in handpiece 12. Further, camera 56 and lens arrangement 58 are sealed in protective housing 60 which prevents moisture damage to the optics and electronics contained therein.

A problem, not limited to the medical and dental fields but to any application where monitoring and limiting of contamination is important, is how to prevent an endoscope from carrying contamination into the work area. Although the immersibility of handpiece 12 goes far to prevent such transfer of contaminants, the present apparatus provides a sheath 102, shown in FIG. 9a and 9b capable of completely isolating handpiece 12 from the work are. Sheath 102, shown in FIG. 9a, both prevents carrying of contaminants from one work area to another and aids in keeping handpiece 12 in clean operating condition.

FIG. 9a shows sheath 102 ready to be installed onto handpiece 12. Sheath 102, fabricated of optically clear elastic PVC material or similar substitute, is sized just small in diameter, and just shorter in length than the corresponding measurements for handpiece 12. Sheath 102 is provided with a collar 104 of a firm elastic material designed to fit into groove 38. FIG. 9b shows sheath 102 installed on handpiece 12, stretched to fit snugly over it. Collar 104 is seated into groove 38 serving to retain sheath 102 in place. It is readily apparent that since the shape and size of objective element 66 varies according to the particular application, sheath 102 is available in a variety of shapes and sizes.

In operation, the user cleans handpiece 12 by immersing it into a sterilizing bath, then installs an unused sheath 102 in place. Handpiece 12 is then used is the manner described above. When the procedure is completed sheath 102 is removed and discarded, and handpiece 12 cleaned and stored for its next use.

In general, to those skilled in the art to which this invention relates, many changes in construction and widely differing embodiments and applications of the present invention will suggest themselves without departing from its spirit and scope. For example, the overall shape of handpiece 12 is virtually infinitely variable to suit particular applications, as is the shape, size and function of the possible objective elements which may be used. Further, many optical and electrical substitutions may be made in the above described embodiment without changing the basic function or purpose of the present invention. Thus the disclosures and desciptions herein are purely illustrative and are not intended to be in any sense limiting.

What is claimed is:

1. A video imaging device for presenting an image of a selected objective at a selected circular orientation, comprising:
    a body member;
    means carried by said body member capable of rotatably presenting an image for monitoring; and
    means removably attached to said means for presenting an image for monitoring for selectively directing the focus of said means for presenting an image to a monitor.

2. A video imaging device for presenting an image of a selected objective at a selected circular orientation, comprising:
    a body member;
    means carried by said body member capable of rotatably presenting an image to a video monitor; and
    means removably attached to said means for presenting an image to a video monitor for selectively directing the focus of said means for presenting an image to a video monitor.

3. A video imaging device for presenting an image of a selected objective at a selected circular orientation, comprising:
    a hand manipulable body member;
    means carried by said body member capable of presenting an image to a monitor whereby said image may be selectively rotated up to 360 degrees; and
    means removably attached to said means for presenting an image to a monitor for selectively directing the focus of said means for presenting an image to a monitor.

4. The video imaging apparatus according to claim 3, wherein means removably attached to said means for presenting an image to a video monitor comprises a modular objective element.

5. The video imaging apparatus according to claim 4, wherein said modular objective element comprises means for selectively directing the focus of said video imaging apparatus.

6. The video imaging apparatus according to claim 5, wherein said means for selectively directing the focus of said video imaging apparatus comprises a minor and lens.

7. The video imaging apparatus according to claim 3, wherein said means for presenting an image to a monitor is capable of providing said image to a video monitor.

8. The video imaging apparatus according to claim 7, wherein said body member is a longitudinal member and wherein said video imaging apparatus further includes means for presenting to a video monitor an image located at a selected angle to the longitudinal axis of said body member.

9. The video imaging apparatus according to claim 7 further comprising a light source carried by said body member.

10. The video imaging apparatus according to claim 9, wherein said light source carried by said body member extends into said means removably attached to said means for presenting an image to a video monitor for selectively directing the focus of said means for presenting an image to a video monitor.

11. The video imaging apparatus according to claim 7, wherein said means for presenting an intraoral image to a video monitor includes a charge-coupled device imaging means.

12. The video imaging apparatus according to claim 11, wherein said charge-coupled device imaging means further includes means capable of generating a simulated color image.

13. The video imaging apparatus according to claim 7, further comprising means facilitating the immersion of the video imaging means in a sterilizing liquid while preventing contact of the sterilizing liquid with the charge-coupled device imaging means.

14. A modular objective element carrying image directing means adapted to be removably installed on the distal end of an endoscope for transmitting an image of an object to the endoscope.

15. The modular objective element according to claim 14 wherein said objective element further comprises means for bending the image path of said object into view of said endoscope.

16. The modular objective element according to claim 15, wherein said for bending the image path if said object comprises a mirror and lens.

17. A video imaging device for presenting an image of a selected objective which is usable with endoscopic processing equipment, comprising:
 a body member;
 means carried by said body member capable of presenting an image for video monitoring which is fittable and maneuverable within a patient's mouth; and
 means attached to said means for presenting an image for selectively directing the focus of said means for presenting an image.

18. The video imaging device of claim 17, wherein said means for presenting an image is capable of rotatably presenting the image.

19. The video imaging device of claim 17, wherein said means for directing the focus is removably attached to said means for presenting an image.

* * * * *

REEXAMINATION CERTIFICATE (1734th)
United States Patent [19]
Milbank et al.

[11] B1 4,858,001
[45] Certificate Issued Jun. 30, 1992

[54] MODULAR ENDOSCOPIC APPARATUS WITH IMAGE ROTATION

[75] Inventors: Miles C. Milbank, San Ramon; Perry M. Williams, San Carlos, both of Calif.

[73] Assignee: High-Tech Medical Instrumentation, Inc., Dublin, Calif.

Reexamination Request:
No. 90/002,046, Jun. 8, 1990

Reexamination Certificate for:
Patent No.: 4,858,001
Issued: Aug. 15, 1989
Appl. No.: 106,742
Filed: Oct. 8, 1987

[51] Int. Cl.$^5$ ............... H04N 7/18; A61B 1/04; A61B 1/06
[52] U.S. Cl. ............... 358/98; 128/6; 356/241; 358/225; 358/229; 433/29
[58] Field of Search ............... 358/229, 87

[56] References Cited

U.S. PATENT DOCUMENTS

| | | | |
|---|---|---|---|
| 3,505,465 | 4/1970 | Rees | 358/87 |
| 3,557,780 | 1/1971 | Sato | 128/4 |
| 4,074,306 | 2/1978 | Kakinuma et al. | 128/6 |
| 4,341,518 | 7/1982 | Wallace . | |
| 4,403,956 | 9/1983 | Nakanishi . | |
| 4,491,965 | 1/1985 | Danna et al. | 128/4 |
| 4,539,586 | 9/1985 | Danna et al. . | |
| 4,575,805 | 12/1986 | Moermann et al. . | |
| 4,594,608 | 6/1986 | Hatae et al. . | |
| 4,626,905 | 12/1986 | Schmidt | 358/229 |
| 4,667,656 | 5/1987 | Yabe . | |
| 4,727,859 | 3/1988 | Lia | 128/6 |
| 4,753,595 | 6/1988 | Schuss et al. . | |
| 4,790,751 | 12/1988 | Reinhardt et al. . | |
| 4,917,603 | 4/1990 | Haack . | |

FOREIGN PATENT DOCUMENTS

| | | |
|---|---|---|
| 2505798 | 2/1975 | Fed. Rep. of Germany . |
| 53-45081 | 4/1978 | Japan . |

*Primary Examiner*—Howard W. Britton

[57] ABSTRACT

A hand held endoscopic apparatus consists of a body, a camera and a removable and interchangeable objective element capable of presenting an image of an object to the camera. The objective element may be either rigid, or deformable, and may enable viewing of an image at varying angles to the longitudinal axis of the handpiece. The endoscope is capable of presenting an image for real-time viewing or for recording and play back at a later time. The camera is rotatably mounted within the body to allow rotation of the image presented for viewing. The endoscope is fully immersible in liquid media, for example sterilizing liquid, and is provided with an optically transparent sheath capable of isolating the endoscope from the working environment.

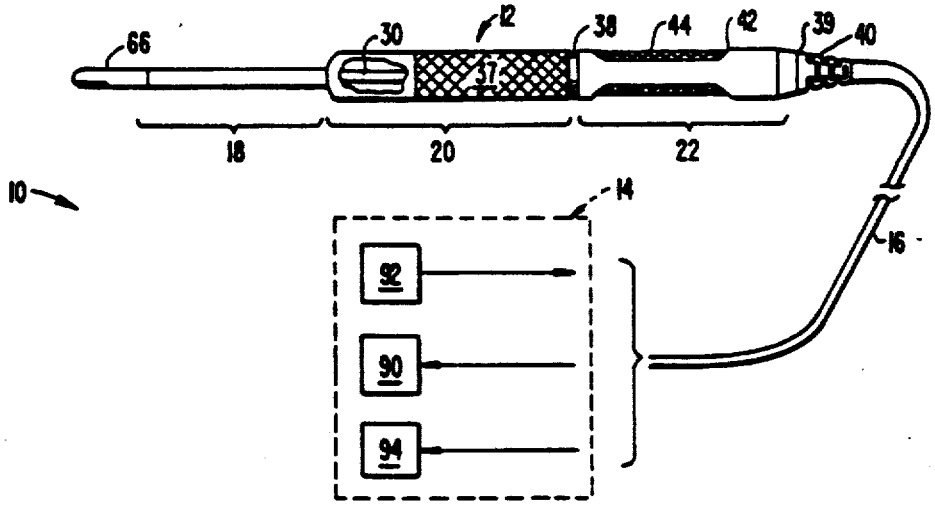

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 14–19 are cancelled.

Claims 1–4 and 6 are determined to be patentable as amended.

Claims 5 and 7–13, dependent on an amended claim, are determined to be patentable.

New claims 20–41 are added and determined to be patentable.

1. [A] *An endoscopic* video imaging device for presenting an image of a selected objective at a selected circular orientation, comprising:
   a body member;
   means carried by said body member [capable of] *for* rotatably presenting an image *of a selected object* for monitoring; and
   means removably attached to said means for presenting an image for monitoring for selectively directing the focus of said means for presenting an image to a monitor.

2. [A] *An endoscopic* video imaging device for presenting an image of a selected objective at a selected circular orientation, comprising:
   a body member;
   means carried by said body member [capable of] *for* rotatably presenting an image *of a selected object* to a video monitor; and
   means removably attached to said means for presenting an image to a video monitor for selectively directing the focus of said means for presenting an image to a video monitor.

3. A *dental endoscopic* video imaging [device] *apparatus* for presenting an image of a selected objective at a selected circular orientation, comprising:
   a hand manipulable body member;
   means carried by said body member [capable of] *for* presenting an image *of a selected object* to a monitor whereby said image may be selectively rotated up to 360 degrees; and
   means removably attached to said means for presenting an image to a monitor for selectively directing the focus of said means for presenting an *intraoral* image to a monitor.

4. The video imaging apparatus according to claim 3, wherein *said* means removably attached to said means for presenting an image to a video monitor comprises a modular objective element.

6. The video imaging apparatus according to claim 5, wherein said means for selectively directing the focus of said video imaging apparatus comprises a [minor] *mirror* and lens.

20. *An endoscopic optical imaging device comprising:*
   *a body member;*
   *a sensor for sensing an image of a selected target and sending a signal indicative of the image to a monitor, said sensor being coupled to said body member;*
   *an objective element coupled to said body member and arranged to focus an image of a selected target upon said sensor; and*
   *means for producing relative rotation between said sensor and said objective element to rotatably present the image of the selected target to the monitor.*

21. *The optical imaging device of claim 20 wherein said means for producing relative rotation is capable of rotating the image of the selected target 180 degrees.*

22. *The optical imaging device of claim 20 wherein said objective element includes optic elements that are arranged to bend the path of the image of the selected target at least 30 degrees.*

23. *The optical imaging device of claim 20 wherein said objective element is removably coupled to said body member.*

24. *An endoscopic optical imaging device comprising:*
   *a body member;*
   *a camera disposed in said body member, said camera being rotatably coupled to said body member; and*
   *an objective element coupled to said body member and arranged to focus an image of a target upon said camera.*

25. *The optical imaging device of claim 24 further including means for rotating said camera relative to said body member.*

26. *An optical imaging device comprising:*
   *an elongated member having an elongated bore and including a proximal portion, a distal portion, and an intermediate portion between said proximal and distal portions;*
   *a shaft having a longitudinal axis and being disposed in said bore, said shaft being rotatably coupled to said elongated member;*
   *a sensor for sensing an image of a selected target and sending a signal indicative of the image to a processor, said sensor being fixedly secured to said shaft;*
   *an objective element coupled to the distal end of said elongated member and arranged to focus an image of a selected target toward said sensor.*

27. *The optical imaging device of claim 26 wherein the proximal portion of said elongated member includes an opening in its peripheral surface that provides access to said shaft such that the shaft can be rotated.*

28. *The optical imaging device of claim 27 further including means for preventing said shaft from bending about said longitudinal axis.*

29. *The optical imaging device of claim 28 wherein said preventing means comprises O-rings positioned between said shaft and said elongated member.*

30. *A dental endoscopic apparatus comprising:*
   *a rigid elongated handpiece having a proximal end and a distal end;*
   *a flexible cable having one end coupled to said proximal end and another end adapted for coupling to video imaging equipment;*
   *a housing removably coupled to said distal end of said rigid elongated handpiece;*
   *a sensor for sensing an image of a selected target, said sensor being coupled to said rigid elongated handpiece* and said flexible cable, said sensor extending into said housing;

opto-electrical componentry extending from said sensor through said handpiece to said cable; and an objective element positioned in said housing and arranged to focus an image of a selected target upon said sensor when said housing is coupled to said rigid elongated handpiece.

31. The dental endoscopic apparatus of claim 30, further including an optically clear casing that is coupled to said handpiece and sealingly encases said sensor, a tubular member that surrounds the opto-electrical componentry that extends from said sensor to said flexible cable, and seals disposed between said tubular member and said handpiece.

32. The dental endoscopic apparatus of claim 30 wherein said sensor is rotatably coupled to said handpiece.

33. A dental endoscopic apparatus comprising:

an elongated handpiece having a proximal end and a distal end, said distal end adapted to fit and be maneuvered in a patient's mouth, said elongated handpiece being rigid along its length from said proximal end to said distal end;

a flexible cable having first and second ends, said first end being coupled to said proximal end of said rigid elongated handpiece and said second end adapted for coupling to video imaging equipment;

a sensor for sensing an image of a selected intraoral target and generating a signal indicative of said image, said sensor being coupled to said handpiece;

an objective element coupled to said distal end of said rigid elongated handpiece and arranged to focus an image of a selected intraoral target upon said sensor;

opto-electrical componentry for transmitting said signal to video imaging equipment, said opto-electrical componentry extending from said sensor through said rigid elongated handpiece to said flexible cable; and means for changing the orientation of said sensor without displacing said flexible cable.

34. The apparatus of claim 33 wherein said orientation changing means includes means for producing relative rotation between said objective element and said sensor.

35. The apparatus of claim 33 wherein said orientation changing means permits 180 degree rotation of said sensor without displacing said flexible cable.

36. The apparatus of claim 33 wherein said orientation changing means permits 360 degree rotation of said sensor about the longitudinal axis of said elongated member.

37. The apparatus of claim 33 wherein said orientation changing means permits 360 degree rotation of said sensor relative to said first end of said cable without displacing said cable.

38. The apparatus of claim 33 wherein said elongated handpiece is essentially inflexible along its length between said proximal and distal ends.

39. The apparatus of claim 33 wherein said cable terminates at said proximal end of said rigid elongated handpiece.

40. The apparatus of claim 33 wherein the distance between the proximal and distal ends of said rigid elongated handpiece is at least 50 mm.

41. A dental endoscopic apparatus comprising:

an elongated handpiece having a proximal end and a distal end, said distal end adapted to fit and be maneuvered in a patient's mouth, said elongated handpiece being rigid along its length from said proximal end to said distal end;

a flexible cable having first and second ends, said first end being coupled to said proximal end of said rigid elongated handpiece and said second end adapted for coupling to video imaging equipment;

a sensor for sensing an image of a selected intraoral target and generating a signal indicative of said image, said sensor being coupled to said handpiece;

an objective element coupled to said distal end of said rigid elongated handpiece and arranged to focus an image of a selected intraoral target upon said sensor;

opto-electrical componentry for transmitting said signal to video imaging equipment, said opto-electrical componentry extending from said sensor through said rigid elongated handpiece to said flexible cable; and means for rotating said elongated handpiece relative to said flexible cable without flexing, rotating or twisting said flexible cable.

* * * * *